United States Patent [19]

Katsumata et al.

[11] Patent Number: 5,559,016
[45] Date of Patent: Sep. 24, 1996

[54] PROCESS FOR PRODUCING ALANINE

[75] Inventors: Ryoichi Katsumata; Shin'ichi Hashimoto, both of Machida, Japan

[73] Assignee: Kyowa Hakko Kogyo Co., Ltd., Tokyo, Japan

[21] Appl. No.: 170,936

[22] Filed: Dec. 21, 1993

[30] Foreign Application Priority Data

Dec. 22, 1992 [JP] Japan ................. 4-342709

[51] Int. Cl.$^6$ ................ C12P 13/06; C12N 1/21; C12N 15/53; C12N 9/02
[52] U.S. Cl. ............... 435/116; 435/252.32; 435/252.33; 435/320.1; 435/69.1; 435/189; 435/191; 536/23.2; 536/23.7; 935/60
[58] Field of Search .................. 435/116, 189, 435/191, 252.32, 252.33, 69.1, 320.1; 536/23.2, 23.7; 935/60, 14

[56] References Cited

FOREIGN PATENT DOCUMENTS 60-184393 9/1985 Japan .
62-36196 2/1987 Japan .............................. C12P 13/06

OTHER PUBLICATIONS

Goodfellow, M. et al. 1983. In: *The Biology of the Actinomycetss,* ed. M. Goodfellow et al, Academic Press, London, pp. 40–46 and 77–79.

Metzler, D. E. 1977. *Biochemistry,* Academic Press, New York NY, pp. 550–551.

Kuroda, S. et al. 1990. Biochem vol. 29 pp. 1009–1015.

Hashimoto, S. et al 1993. Biotechnol. Let. vol. 15 pp. 1117–1122.

Arcuri, E. J. et al. 1988. Soc. Indust. Microbiol, 1988 Ann. Mtg. vol. 4 p. 33.

De Boer, L. et al. 1989. Antonie van Leeuwenhoek vol. 56 pp. 221–232.

Soda et al, "Alanine", Chemical Abstracts 104(15):565 (1986).

Sakamoto et al, "Gene cloning, purification and characterization of thermostable alanine dehydrogenase of *Bacillus stearothermophilus*", J. Ferment. Bioeng. 69(3):154–158 (1990).

*Primary Examiner*—Mary E. Mosher
*Attorney, Agent, or Firm*—Nixon & Vanderhye P.C.

[57] ABSTRACT

A process for producing alanine which comprises culturing in a medium a microorganism belonging to the genus Escherichia, Corynebacterium or Brevibacterium which has an L-alanine dehydrogenase activity and is capable of producing alanine, allowing the microorganism to produce and accumulate alanine in the culture medium, and recovering alanine from the culture medium.

8 Claims, 2 Drawing Sheets

5,559,016

PROCESS FOR PRODUCING ALANINE

FIELD OF THE INVENTION

This invention relates to a process for producing DL-, L- or D-alanine by fermentation. DL-Alanine is an important amino acid which is used in the field of food industry and the like, as well as L-alanine in pharmaceutical and food industries and D-alanine in pharmaceutical industry.

BACKGROUND OF THE INVENTION

The known methods of producing DL-alanine include a synthetic method making use of the Strecker reaction in which acetaldehyde, prussic acid and ammonia are used as starting materials, a production method in which a sugar is fermented by *Microbacterium ammoniaphilum* (JP-A-50-10028; the term "JP-A" as used herein means an "unexamined published Japanese patent application"). L-Alanine is generally produced by an enzymatic process such as a process in which L-aspartic acid is decarboxylated with an enzyme (JP-B-46-7560 corresponding to U.S. Pat. No. 3,458,400; the term "JP-B" as used herein means an "examined published Japanese patent application") or a process in which lactic acid and an amino donor is fermented by a D-alanine auxotrophic *Escherichia coli* strain (JP-A-62-36196), or by a process in which a sugar is fermented by *Corynebacterium tumescens* (JP-B-36-14298). The present inventors have also applied a process for producing L-alanine comprising fermenting a sugar by a strain belonging to the genus Arthrobacter (International Application JP91-01574 corresponding to EP-A-0 567 644). Known processes for the production of D-alanine include a process in which DL-alanineamide is hydrolyzed using a D-amidase obtained from a strain belonging to the genus Arthrobacter to form D-alanine and L-alanineamide, and the thus formed D-alanine is isolated from the reaction mixture (JP-A-1-317387 corresponding to EP-A- 0 334 358) and a process in which a sugar is fermented by a D-cycloserine resistant mutant derived from *Brevibacterium lactofermentum* (JP-A-1-187091 corresponding to EP-A-0 310 949 and U.S. Pat. No. 5,254,464).

Further, there is a report that a small amount of alanine can be produced by recombinant DNA techniques using a strain belonging to the genus Zymomonas into which a gene coding for a Bacillus L-alanine dehydrogenase is introduced [*Appl. Environ. Microbiol.*, 57, 1360 (1991)].

Great concern has been directed toward the development of a process for economically and industrially producing DL-alanine which is useful as a food additive, L-alanine which is useful as a food additive and a component of amino acid infusion and D-alanine which is useful in the field of pharmaceutical industry.

DL-alanine can be economically produced by chemical synthesis through the Strecker reaction, but this process is not necessarily desirable since DL-alanine is used as a food additive and, in the Strecker reaction, toxic cyanogen is used.

When optically active L- or D-alanine is required, an enzymatic or fermentation process which does not require optical resolution operation is economically advantageous in comparison with chemical synthesis processes that require such a complex operation. Fermentation processes are especially advantageous from the industrial point of view, because inexpensive sugars can be used as the starting material. Prior art processes for the fermentation production of alanine are not industrially useful because of such disadvantages as low yield and low accumulation level in the culture medium. The present inventors previously found that a microorganism belonging to the genus Arthrobacter and having reduced or deleted alanine racemase activity can ferment a sugar to produce and accumulate a significant amount of L-alanine (International Application JP91-01574). Though the yield of alanine obtained according to this method is sufficiently high, it is disadvantageous in that it requires a long period of fermentation and it is difficult to separate and purify alanine from fetid substances which are produced during the fermentation.

SUMMARY OF THE INVENTION

An object of the present invention is to provide a process for producing alanine simply and economically on an industrial scale.

The above object can be attained by a process for producing alanine which comprises culturing in a medium a microorganism belonging to the genus Escherichia, Corynebacterium or Brevibacterium which has L-alanine dehydrogenase activity and is capable of producing alanine, allowing the microorganism to produce and accumulate alanine in the culture medium, and recovering alanine from the culture medium.

More particularly, the present invention provides a process for producing DL-, L- or D-alanine which comprises culturing in a medium a microorganism, belonging to the genus Escherichia, Corynebacterium or Brevibacterium, transformed with a recombinant DNA molecule comprising an L-alanine dehydrogenase gene, for example, cloned from a microorganism belonging the genus Arthrobacter, under conditions such that the gene is expressed and the transformed microorganism thereby forms and accumulates DL-, L- or D-alanine in the culture medium. DL-, L- or D-Alanine is then recovered from the culture medium.

DETAILED DESCRIPTION OF THE INVENTION

Figure 1:
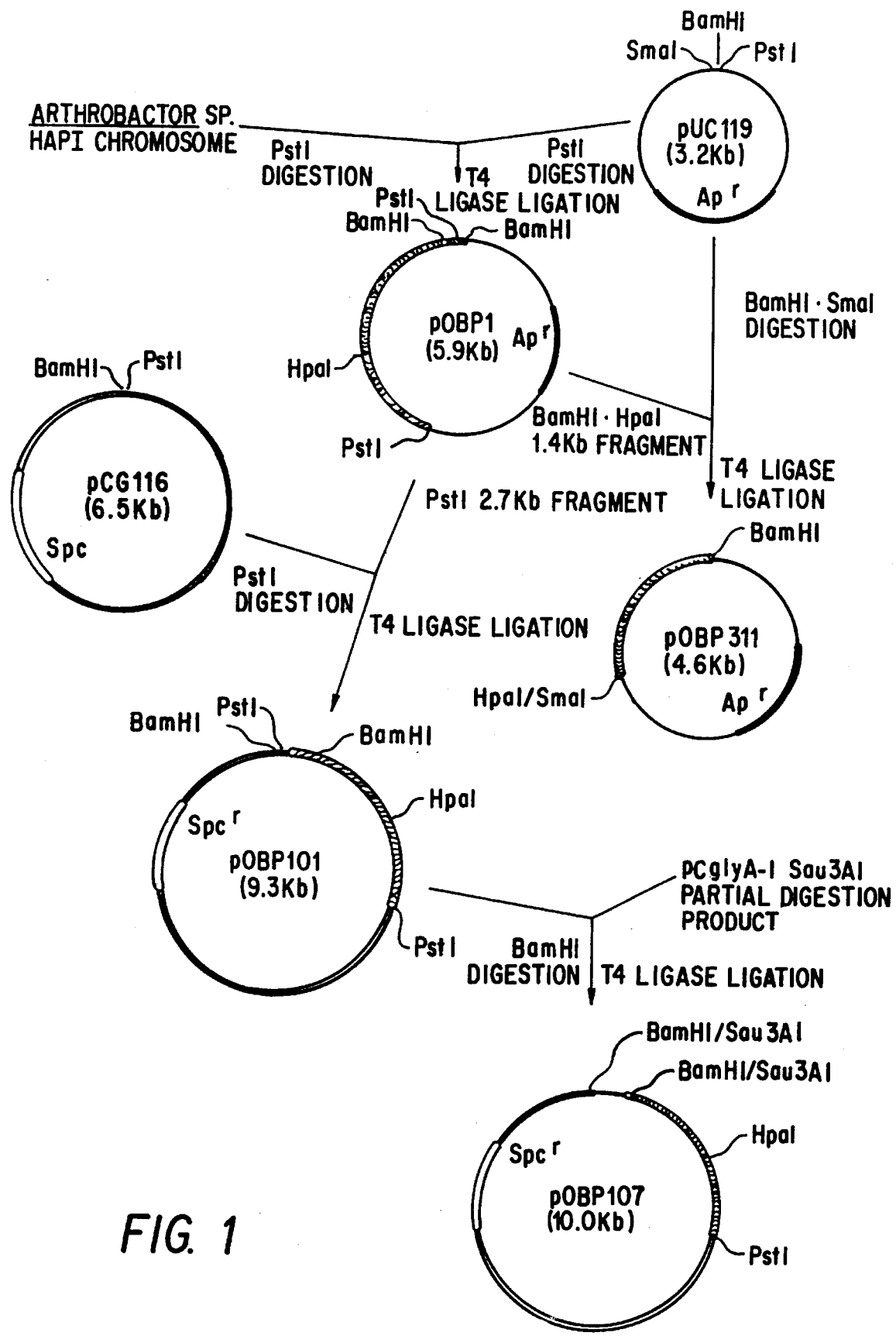
FIG. 1 shows restriction cleavage maps and construction scheme of pOBP1, pOBP311, pOBP101 and pOBP107.

The present invention retales to a transformed microorganism having L-alanine dehydrogenase activity resulting from the introduction of an L-alanine dehydrogenase gene. The L-alanine dehydrogenase gene can be cloned and introduced into a vector, for example, a plasmid, using recombinant DNA techniques.

Any known *Escherichia coli* strains may be used as the host microorganism belonging to the genus Escherichia, with preferred examples of the strains including JM105 [*Gene*, 33, 103, (1985)], MM294 [*Cloning Vectors, A Laboratory Manual* (1985)] and HB101 and W3110 [*Molecular Cloning, A Laboratory Manual,* Cold Spring Harbor Laboratory Press (1982); hereinafter referred to as "*Molecular Cloning*"].

Any microorganism known as Coryneform glutamic acid producing strains may be used as the host microorganism belonging to the genus Corynebacterium or Brevibacterium, but the following strains are preferred hosts:

*Corynebacterium glutamicum* ATCC 13032

*Corynebacterium acetoacidophilum* ATCC 13870
*Corynebacterium herculis* ATCC 13868
*Corynebacterium lilium* ATCC 15990
*Corynebacterium melassecola* ATCC 17965
*Brevibacterium divaricatum* ATCC 14020
*Brevibacterium flavum* ATCC 14067
*Brevibacterium immariophilum* ATCC 14068
*Brevibacterium lactofermentum* ATCC 13869
*Brevibacterium thiogenitalis* ATCC 19240

Auxotrophic and/or drug resistant mutants derived from these microorganisms can be used as hosts.

Any microorganism can be used as the source of the L-alanine dehydrogenase gene as long as it has L-alanine dehydrogenase activity. The gene is preferably obtained from a procaryote, such as a bacterial strain belonging to the genus Arthrobacter or Bacillus or actinomycetes. An illustrative example of such a strain is Arthrobacter sp. HAP1 (deposited under the terms of the Budapest Treaty on Nov. 8, 1991, in Fermentation Research Institute, Agency of Industrial Science and Technology, 1-3, Higashi 1-chome, Tsukuba-shi, Ibaraki 305 JAPAN, Accession No. FERM BP-3644; International Application JP91-01574).

The gene sequence can be inserted into any of a variety of vectors that can autonomously replicate in the host microorganism. For example, pBR322 [*Gene*, 2, 95 (1977)], pUC119 (Takara Shuzo Co., Ltd.), pACYC177 [*Cloning Vectors, A Laboratory Manual* (1985)] and like plasmids can be used when *E. coli* is a host; pCG1 (JP-A-57-134500 corresponding to EP-A-0 058 889), pCG2 (JP-A-58-35197 corresponding to EP-A-0 073 062), pCG4, pCG11 (both disclosed in JP-A-57-183799 corresponding to EP-A-0 063 763), pCG116, pCE54, pCB101 (all of three in JP-A-58-105999 corresponding to EP-A-0 082 485), pCE51, pCE52, pCE53 [all of three in *Mol. Gen. Genet.*, 196, 175 (1984)] and like plasmids can be used when a bacterial strain belonging to the genus Corynebacterium or Brevibacterium is used as the host.

Recombination of a donor DNA molecule containing the L-alanine dehydrogenase-encoding sequence with a vector DNA molecule can be carried out by known methods [*Methods in Enzymology*, 68 (1979)]. Both of the DNA molecules can be digested in vitro with appropriate restriction enzymes and the resulting fragments are ligated using a DNA ligase directly or after treatment of the digested terminus with a terminal transferase or a DNA polymerase, with production of a mixture of recombinant products. A recombinant DNA molecule which contains the L-alanine dehydrogenase-encoding gene can be obtained by transforming an *E. coli* strain (MM294, for example) with the thus obtained mixture of recombinant products, selecting a transformant having L-alanine dehydrogenase activity and then isolating the recombinant molecule from the transformant that includes the L-alanine dehydrogenase encoding sequence.

Transformation of *E. coli* can be carried out by the known calcium chloride method (*Molecular Cloning*), and microorganisms belonging to the genus Corynebacterium or Brevibacterium can be transformed by the protoplast method (JP-A-57-186492 and JP-A-57-18649 corresponding to EP-A-0 063 764). One skilled in the art will appreciate that other art recognized protocols can also be used.

A recombinant DNA molecule containing an L-alanine dehydrogenase encoding sequence can be integrated into the chromosome of a host microorganism. Such integration can be carried out, for example, according to the method disclosed in *Gene*, 107, 61 (1991), by preparing a recombinant DNA in which a region related to the autonomous replication function in the host microorganism (replicon) is deleted. The host microorganism is then transformed with the resulting recombinant DNA. Alternatively, the method disclosed in *Bio/Technology*, 9, 84 (1991) can be used which involves inserting the L-alanine dehydrogenase gene into a vector which cannot autonomously replicate in the host microorganism so as to construct a recombinant DNA molecule. The resulting molecule can be introduced into a host microorganism belonging to the genus Corynebacterium or Brevibacterium from an other bacterial strain such as *E. coli* by means of conjugation transfer.

The L-alanine dehydrogenase gene can be efficiently expressed in a host microorganism by operably linking a promoter, operative in the host microorganism, to the L-alanine dehydrogenase encoding sequence. The promoter is preferably inserted into an upstream region of the L-alanine dehydrogenase encoding sequence. Promoters suitable for use in *E. coli* include the lactose operon promoter, the tryptophanase gene promoter, or the like. When a bacterial strain belonging to the genus Corynebacterium or Brevibacterium is used as the host, chromosomal DNA of such a strain can be digested with a restriction enzyme. Alternatively, plasmid DNA containing a gene expressed at a high level in Corynebacterium or Brevibacterium can be subjected to restriction enzyme digestion. In either case, resulting DNA fragments having promoter activity can be introduced into an expression vector, for example, a plasmid, in operable linkage with an L-alanine dehydrogenase gene. The resulting recombinant molecule can then be used to transform a strain belonging to the genus Corynebacterium or Brevibacterium and resulting transformants which produce L-alanine dehydrogenase at a high level can be selected. An example of a plasmid containing a gene which is known to be expressed at a high level in a strain belonging to the genus Corynebacterium or Brevibacterium is the plasmid pCglyA-1 (JP-A-2-42994) contained in *Corynebacterium glutamicum* K75 (FERM BP-1874).

DL-, L- or D-alanine can be produced by culturing the thus obtained and selected strain belonging to the genus Escherichia, Corynebacterium or Brevibacterium in accordance with methods commonly used for amino acid fermentation production. That is, transformants are cultured in a medium containing carbon sources, nitrogen sources, inorganic compounds, amino acids, vitamins and the like under aerobic or anaerobic conditions while controlling temperature, pH and the like to allow DL-, L- or D-alanine to be produced and accumulated in the culture medium. The product is then recovered.

Carbon sources suitable for used in the present invention are those that the host microorganism can assimilate. Typical examples including carbohydrates such as glucose, fructose, sucrose, maltose, mannose, glycerol, starch, starch hydrolyzate, molasses and the like, polyalcohols and various organic acids such as pyruvic acid, fumaric acid, lactic acid, acetic acid and the like.

Suitable nitrogen sources include ammonia and its inorganic and organic salts such as ammonium chloride, ammonium sulfate, ammonium carbonate, ammonium acetate and the like and urea and other nitrogen-containing compounds, nitrogen-containing organic substances such as peptone, NZ-amine, meat extract, yeast extract, corn steep liquor, casein hydrolyzate, fish meal, fish meal digest and the like.

Suitable inorganic compounds include potassium dihydrogenphosphate, dipotassium hydrogenphosphate, ammonium sulfate, ammonium chloride, magnesium sulfate, sodium chloride, ferrous sulfate, manganese sulfate, calcium carbonate and the like. Though vitamins and amino acids vary depending on the carbon sources, nitrogen sources and the like to be used in the medium, biotin, thiamine, glutamic acid and the like may be used. When the strain to be cultured requires specific substances for its growth, such substances are added to the medium.

The culturing may be carried out under an aerobic condition such as shaking culture, aeration/agitation culture or the like or under an anaerobic condition such as static culture or the like, depending on the oxygen demand of the host microorganism. In some cases, improved productivity can be obtained by starting the culturing under aerobic conditions until growth of the strain reaches an appropriate stage and then continuing the culturing with shaking or aeration/agitation under an oxygen supply-limited condition. The culturing may be carried out at 20° to 50° C. It is desirable to control the pH of the medium at around neutral level. DL-, L- or D-alanine is typically accumulated in the medium within a period of 1 to 5 days.

After completion of the culturing, cells can be removed from the culture broth and the resulting culture supernatant subjected to known purification means such as concentration crystallization, active carbon treatment, ion exchange resin treatment and the like, thereby effecting isolation and recovery of DL-, L- or D-alanine.

Thus, DL-, L- or D-alanine can be produced at a high yield and within a short period of culturing using a strain belonging to the genus Escherichia, Corynebacterium or Brevibacterium that has L-alanine dehydrogenase activity. Since these strains do not produce odor-producing materials, alanine purified therefrom is free from the prior art problems of contamination with odor-producing materials, for example, as found when strains belonging to the genus Arthrobacter are used. Thus, the present method provides a product of high quality.

The following Example is provided to further illustrate the present invention, but is not to be construed as limiting the scope of the invention.

The production of D-alanine is not exemplified in the following example. However, D-alanine can be produced, for example, by transforming D-alanine-producing microorganism as described in JP-A-1-187091 (EP-A-0 310 949) with a recombinant plasmid containing the L-alanine dehydrogenase gene according to the present invention, such as pOBP107, culturing said transformant and purifing the product recovered from the culture medium in the same manner as described in the following example.

EXAMPLE (1) Preparation of Arthrobacter sp. HAP1 chromosomal DNA

A 20 ml portion of a seed culture of Arthrobacter sp. HAP1 obtained by culturing it in an NBG medium (20 g of bouillon powder, 5 g of yeast extract and 10 g of glucose dissolved in 1 liter of water, pH 7.2), was inoculated into 400 ml of fresh NBG medium and cultured at 30° C. for 10 hours with shaking.

Cells were collected from the resulting culture broth, washed with a TES buffer [0.03M tris(hydroxymethyl)aminomethane (hereinafter referred to as "Tris"), 0.005M disodium ethylenediaminetetraacetate (hereinafter referred to as "EDTA"), 0.05M NaCl, pH 8.0] and then suspended in 10 ml of a lysozyme solution (25% sucrose, 0.1M NaCl, 0.05M Tris, 0.4 mg/ml lysozyme, pH 8.0), followed by incubation at 30° C. for 30 minutes. Thereafter, chromosomal DNA was isolated from the collected cells according to the procedure of Saito and Miura [Biochim. Biophys. Acta, 72, 619 (1963)].

(2) Cloning of Arthrobacter sp. HAP1 L-alanine dehydrogenase gene

In the following studies, all of the in vitro experiments for DNA digestion with restriction enzymes and DNA ligation with a DNA ligase were carried out using restriction enzymes and T4 DNA ligase manufactured by Takara Shuzo Co., Ltd. under the reaction conditions recommended by the manufacturer.

Plasmid pUC119 was purchased from Takara Shuzo Co., Ltd. and used as a vector for an E. coli host. Isolation of plasmids from E. coli strains containing these plasmids or variants thereof was carried out by the procedure of Maniatis et al. (Molecular Cloning).

Transformation of E. coli was carried out by the procedure also disclosed in Molecular Cloning.

Three μg of the Arthrobacter sp. HAP1 chromosomal DNA obtained by the procedure described in (1) above and 1 μg of the plasmid pUC119 were each digested completely with PstI, and the resulting fragments were allowed to react with T4 DNA ligase. The thus obtained ligation reaction mixture was used to transform E. coli strain MM294.

Transformants containing the L-alanine dehydrogenase gene were selected by the procedure disclosed in Biochem., 25, 3268–3274 (1986).

Namely, cells of the strain MM294 transformed with the above-mentioned ligation reaction mixture were spread on an L agar medium [containing 10 g of Bacto-peptone, 5 g of yeast extract and 5 g of NaCl in 1 liter of water, pH 7 (L medium) supplemented with agar to a final concentration of 1.5%] supplemented with 100 mg/l of ampicillin and cultured overnight at 30° C. Colonies formed on the agar medium were transferred on a nylon membrane filter (Bio Trace™ NT, 82 mm, manufactured by Gelman Sciences). The transferred agar medium was stored as the master plate. The filter was put on a freshly prepared L agar plate and incubated at 30° C. for 3 hours and then at 57° C. for 10 minutes. The filter was removed from the L agar plate and put in a glass dish to expose it to toluene vapor for 10 minutes. The resulting filter was put on a filter paper which had been impregnated with a pre-treatment solution consisting of 50 mM of a Gly/KOH/KCl buffer (pH 9.0) and 2.6 mM of NAD (β-nicotinamide adenine dinucleotide), incubated at 30° C. for 1 hour and then transferred on another filter paper that had been impregnated with a staining solution consisting of 50 mM Gly/KOH/KCl buffer (pH 9.0), 1.3 mM NAD, 50 mM L-alanine, 0.128 mM PMS (phenazine methosulfate) and 0.48 mM NBT (Nitro Blue Tetrazolium). After standing at room temperature for 10 minutes, colonies that developed in blue purple color were selected and their corresponding colonies on the master plate were isolated to serve as transformants containing the L-alanine dehydrogenase gene (this technique will be hereinafter called "activity staining").

Presence of the L-alanine dehydrogenase gene in the thus selected transformants was confirmed by measuring L-alanine dehydrogenase activity in the cell extract of each transformant in the following manner. Namely, each of the selected transformants was cultured at 30° C. for 16 hours in 10 ml of L medium, and the resulting cells were collected by centrifugation, suspended in 1 ml of 50 mM phosphate buffer (pH 7.5) and then subjected to ultrasonication. Thereafter, the cell lysate thus obtained was centrifuged at 10,000 rpm for 40 minutes and the resulting supernatant fluid was examined for the L-alanine dehydrogenase activity by the procedure of Ohshima et al. [Eur. J. Biochem., 100, 29–39 (1979)].

Figure 2:
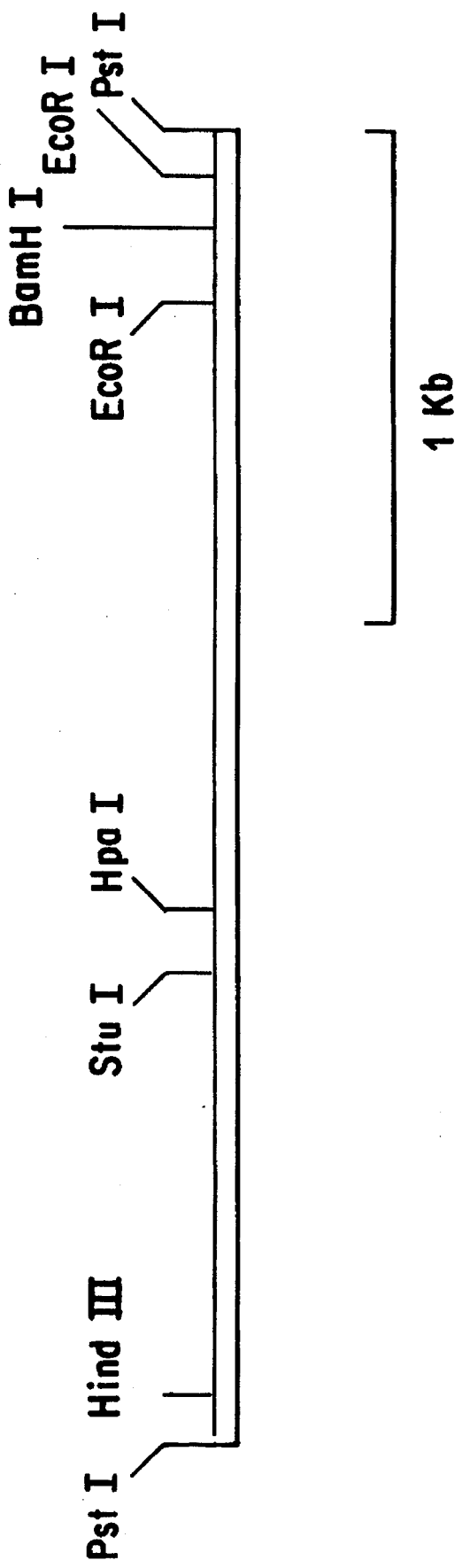
FIG. 2 shows a restriction map of a DNA fragment of about 2.7 kb containing an L-alanine dehydrogenase gene cloned from a strain of Arthrobacter sp. HAP1 into pOBP1.

Plasmid DNA was isolated from a transformant strain in which L-alanine dehydrogenase activity had been confirmed. The thus obtained plasmid, named pOBP1, was found to have an insertion fragment of about 2.7 kilobases (hereinafter referred to as "kb") at the PstI site of the vector pUC119 (see FIG. 1). The insertion DNA fragment was checked for cleavage sites of several restriction enzymes. A restriction cleavage map of the insertion DNA fragment is shown in FIG. 2. The DNA fragment has no EcoRV, BglII, SmaI and SalI cleavage site. In order to find the exact location of the L-alanine dehydrogenase gene on the PstI fragment of about 2.7 kb contained in pOBP1, subcloning of the gene-containing DNA fragment from pOBP1 was carried out. The plasmid pOBP1 was completely digested with BamHI and HpaI and subjected to agarose gel electrophoresis to purify a DNA fragment of about 1.4 kb. A 0.5 μg portion of the thus obtained DNA fragment and 0.5 μg of pUC119 which had been completely digested with BamHI and SmaI were subjected to ligation reaction with T4 DNA ligase. Thereafter, the resulting ligation reaction mixture was used to transform an *E. coli* strain JM105. The L agar medium supplemented with 100 mg/l of ampicillin, 0.1 mM of IPTG (isopropyl-β-D-thiogalactopyranoside) and 40 mg/l of X-Gal (5-bromo-4-chloro-3-indolyl-β-D-galactoside) was used as a selection medium. A white colony formed on the selection medium was selected and cultured, and plasmid DNA was isolated from the cultured cells and named pOBP311.

The pOBP311-containing strain JM105 was cultured for 16 hours in 10 ml of L medium in the presence or absence of 0.1M IPTG, and the resulting cells were collected by centrifugation, suspended in 1 ml of 50 mM phosphate buffer (pH 7.5) and then subjected to ultrasonication. The cell lysate thus obtained was centrifuged at 10,000 rpm for 40 minutes and the resulting supernatant was examined for L-alanine dehydrogenase activity in the same manner as described above. As a result, the L-alanine dehydrogenase activity was detected in the extract of cells cultured in the presence of IPTG but not in those cultured in the absence of IPTG. From these results, it is evident that the L-alanine dehydrogenase gene is located on DNA fragment of about 1.4 kb contained in pOBP311, namely on the DNA fragment of about 1.4 kb between the BamHI site and the HpaI site in the PstI fragment of about 2.7 kb contained in pOBP1 and that transcription of the gene occurs from the BamHI site toward the HpaI site, because expression of the gene is dependent upon IPTG.

(3) Production of DL-alanine using *E. coli* as a host

The *E. coli* strain JM105 was transformed with the thus constructed plasmids pOBP1 and pOBP311 and with pUC119 to obtain transformant strains AL1, AL311 and JM105/pUC119 respectively. The strain AL1 has been deposited since Dec. 15, 1992, in Fermentation Research Institute, Agency of Industrial Science and Technology, of 1-3, Higashi 1-chome, Tsukuba-shi, Ibaraki 305 Japan, as *Escherichia coli* strain K88 (FERM BP-4121) in accordance with the Budapest Treaty.

Each of these strains was cultured at 30° C. for 12 hours in 3 ml of L medium containing 100 mg/l of ampicillin, and 0.15 ml of the culture broth was introduced into a large test tube containing 15 ml of an A1 medium (30 g of glucose, 10 g of $(NH_4)_2SO_4$, 1 g of $KH_2PO_4$, 1 g of $MgCl_2.6H_2O$, 2 mg of $FeSO_4.7H_2O$, 2 mg of $MnSO_4.4$–$6H_2O$ and 100 mg of thiamin hydrochloride in 1 liter of water, pH 7.4) supplemented with 100 mg/l of ampicillin or with 100 mg/l of ampicillin and 0.1 mM of IPTG and cultured at 30° C. for 45 hours. The culture broth thus obtained was subjected to centrifugation and the resulting culture supernatant was checked for its DL-alanine content by high performance liquid chromatography by the OPA post-column derivation method [*Anal. Chem.*, 51, 1338 (1979)]. The results are shown in Table 1. L-Alanine dehydrogenase activity in cultured cells obtained in the same manner is also measured and the results are shown in Table 1. Since DL-alanine production and L-alanine dehydrogenase activity were found only in strains AL1 and AL311 cultured in the presence of IPTG, it is evident that the DL-alanine production of strains AL1 and AL311 depends on the presence of L-alanine dehydrogenase activity.

TABLE 1

| Strain | Addition of IPTG* | Accumulation of DL-alanine (g/l) | Activity of L-alanine dehydrogenase (U/mg protein) |
|---|---|---|---|
| AL1 | − | 0.0 | <0.01 |
|  | + | 2.8 | 0.38 |
| AL311 | − | 0.0 | <0.01 |
|  | + | 2.9 | 0.39 |
| JM105/pUC119 | − | 0.0 | <0.01 |
|  | + | 0.0 | <0.01 |

*: −, IPTG not added; +, IPTG added (4) Introduction of Arthrobacter sp. HAP1 L-alanine dehydrogenase gene into a strain belonging to the genus Corynebacterium or Brevibacterium Plasmid pCG116 can be used as a vector when a strain belonging to the genus Corynebacterium or Brevibacterium is used as a host. The plasmid is constructed by ligating StuI and PstI sites of a *Corynebacterium glutamicum* plasmid pCG11 (JP-A-57-183799) with a linker obtained by digesting M13mp18 RF DNA (Takara Shuzo Co., Ltd.) with EcoRI, rendering both ends blunt with Klenow fragment (*E. coli* DNA polymerase I) and then digesting it with PstI, making use of their blunt and cohesive ends. The plasmid pCG116 has a molecular length of about 6.5 kb, possesses restriction enzyme cleavage sites BglII, PstI, SalI, XbaI, BamHI, SmaI, KpnI and SacI each as a unique one, and gives a phenotype of spectinomycin and/or streptomycin resistance (see FIG. 1).

Isolation of plasmid from a pCG116-containing strain belonging to the genus Corynebacterium or Brevibacterium was carried out in accordance with the procedure disclosed in JP-A- 57-183799.

The plasmid pOBP1 obtained in (2) above was digested with PstI and subjected to agarose gel electrophoresis to purify an insertion DNA fragment of about 2.7 kb. A 10 μg portion of the thus obtained DNA fragment and 10 μg of pCG116 which had been completely digested with PstI were subjected to ligation reaction with T4 DNA ligase. Thereafter, the resulting ligation reaction mixture was used to transform a strain of *Corynebacterium glutamicum*, ATCC 13032.

Transformation of a strain belonging to the genus Corynebacterium or Brevibacterium was carried out in accordance with the procedure disclosed in JP-A-57-186492 and JP-A-57-18649. Namely, a strain belonging to the genus Corynebacterium or Brevibacterium was seed-cultured in an NB medium (20 g of bouillon powder and 5 g of yeast extract in 1 liter of water, pH 7.2), and 4 ml of the seed culture was inoculated into 40 ml of an SSM medium (20 g of glucose, 10 g of $(NH_4)_2SO_4$, 3 g of urea, 1 g of yeast extract, 1 g of $KH_2PO_4$, 0.4 g of $MgCl_2.6H_2O$, 10 mg of $FeSO_4.7H_2O$, 0.2 mg of $MnSO_4.4$–$6H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6Mo_7O_{24}.4H_2O$, 30 μg of biotin and 1 mg of thiamin hydrochloride in 1 liter of water, pH 7.2) and cultured at 30° C. with shaking. When OD value (absorbance at 660 nm measured by a colorimeter manufactured by Tokyo Kodensha) reached 0.2, penicillin G was added to the culture broth to a final concentration of 0.5 U/ml. The culturing was continued until the OD value reached 0.6. The cells were collected and suspended in 10 ml of an RCGP medium (5 g of glucose, 5 g of casamino acid, 2.5 g of yeast extract, 3.5 g of $K_2HPO_4$, 1.5 g of $KH_2PO_4$, 0.41 g of $MgCl_2.6H_2O$, 10 mg of $FeSO_4.7H_2O$, 2 mg of $MnSO_4.4$–$6H_2O$, 0.9 mg of $ZnSO_4.7H_2O$, 0.04 mg of $(NH_4)_6Mo_7O_{24}.4H_2O$, 30 µg of biotin, 2 mg of thiamin hydrochloride, 135 g of disodium succinate and 30 g of polyvinyl pyrrolidone (molecular weight, 10,000) in 1 liter of water, pH 7.6) supplemented with 1 mg/ml of lysozyme to a cell density of $10^9$ cells/ml, and the cell suspension was transfered into an L type test tube and incubated at 30° C. for 16 hours with gentle shaking to effect protoplast formation. A 0.5 ml portion of the thus obtained protoplast suspension was put into a small test tube and centrifuged at 2,500× g for 5 minutes, and the thus collected protoplasts were suspended in 1 ml of a TSMC buffer (10 mM $MgCl_2$, 30 mM $CaCl_2$, 50 mM Tris, 400 mM sucrose, pH 7.5), washed by centrifugation and suspended again in 0.1 ml of TSMC buffer. The thus treated protoplast suspension was mixed with 100 µl of a 1:1 mixture of double concentration TSMC buffer and a solution containing a DNA to be used for transformation. The mixture was further mixed with 0.8 ml of TSMC buffer supplemented with 20% PEG 6,000. Three minutes thereafter, the resulting mixture was further mixed with 2 ml of RCGP medium (pH 7.2) and centrifuged at 2,500× g for 5 minutes to remove supernatant, and the thus sedimented protoplasts were suspended in 1 ml of RCGP medium. A 0.2 ml portion of the resulting suspension was spread on an RCGP agar medium (RCGP medium containing 1.4% agar, pH 7.2) containing 400 µg/ml of spectinomycin and cultured at 30° C. for 7 days. Colonies grown on the agar medium were collected, washed twice by centrifugation with physiological saline and then suspended in 1 ml of physiological saline. The resulting cell suspension was again spread on an NB agar medium (NB medium containing 1.5% agar, pH 7.2) containing 100 µg/ml of spectinomycin and cultured at 30° C. for 2 days to select a spectinomycin resistant transformant.

A plasmid DNA was isolated from cultured cells of the spectinomycin resistant transformant and named pOBP101. The plasmid was subjected to digestion with various restriction enzymes and agarose gel electrophoresis analysis and was confirmed to have the structure shown in FIG. 1.

In order to realize high level expression of the L-alanine dehydrogenase in a strain belonging to the genus Corynebacterium or Brevibacterium, a plasmid was constructed by inserting a DNA fragment showing strong promoter activity in strains belonging to the genus Corynebacterium or Brevibacterium into an upstream region of the gene. As described in (2) above, the L-alanine dehydrogenase gene is located between the BamHI site and the HpaI site on the PstI DNA fragment of about 2.7 kb contained in pOBP101. Transcription of the gene occurs from the BamHI site toward the HpaI site. As a consequence, the BamHi site must be located in an upstream region of the gene which is a convenient region for the insertion of a DNA fragment having promoter activity. The DNA fragment having promoter activity to be inserted was prepared from a plasmid pCglyA-1 (JP-A-2- 42994). Namely, pOBP101 was isolated from a transformant of *Corynebacterium glutamicum* ATCC 13032 and digested completely with BamHI. A 3 µg portion of the DNA digestion product and 10 µg of the other DNA digestion product obtained by Sau3AI partial digestion of pCglyA-1 isolated from *Corynebacterium glutamicum* K75 (FERM BP-1874) were subjected to ligation reaction with T4 DNA ligase. *Corynebacterium glutamicum* ATCC 13032 was transformed with the resulting ligation reaction mixture, and the transformed cells were spread on NB agar medium containing 100 mg/l of spectinomycin and cultured at 30° C. for 2 days. Colonies grown on the agar medium were transferred on a nylon membrane filter (Bio Trace™ NT, 82 mm, manufactured by Gelman Sciences) to carry out activity staining in accordance with the method described in (2) above. A plasmid DNA was isolated from a strain which showed the highest staining response and was named pOBP107. The plasmid was subjected to digestion with various restriction enzymes and agarose gel electrophoresis analysis and was confirmed to have the structure shown in FIG. 1.

(5) Production of DL- or L-alanine using a strain belonging to the genus Corynebacterium or Brevibacterium as a host The plasmids pOBP101, pOBP107 and pCG116 prepared in the above (4) were used to transform *Corynebacterium glutamicum* ATCC 21352 and *Brevibacterium lactofermentum* ATCC 13869. *Corynebacterium glutamicum* ATCC 21352 is a D-alanine auxotrophic mutant derived from *Corynebacterium glutamicum* ATCC 13032. Because of such an auxotrophic nature, D-alanine was added to the culture medium and protoplast regeneration medium to a final amount of 1 g/l used for transformation. As transformants resulting from transformation of *Corynebacterium glutamicum* ATCC 21352 with pOBP101, pOBP107 and pCG116, strains AL101, AL107 and ATCC21352/pCG116 were obtained respectively. Also, as transformants resulting from transformation of *Brevibacterium lactofermentum* ATCC 13869 with pOBP101, pOBP107 and pCG116, strains BL101, BL107 and ATCC13869/pCG116 were obtained respectively. The strain AL107 has been deposited since Dec. 15, 1992, in Fermentation Research Institute, Agency of Industrial Science and Technology, of 1-3, Higashi 1-chome, Tsukuba-shi, Ibaraki 305 Japan, as *Corynebacterium glutamicum* strain K89 (FERM BP-4122), in accordance with the Budapest Treaty.

Each of the thus obtained transformants was cultured at 30° C. for 16 hours in 3 ml of NB medium containing 100 mg/l of spectinomycin, and 0.5 ml of the culture broth was inoculated into a large test tube containing 12.5 ml of an A2 medium (50 g of glucose, 30 g of $(NH_4)_2SO_4$, 1 g of $KH_2PO_4$, 0.5 g of $MgCl_2.6H_2O$, 10 mg of $FeSO_4.7H_2O$, 5 mg of $MnSO_4.4$–$6H_2O$, 30 µg of biotin and 200 mg of thiamine hydrochloride in 1 liter of water, pH 7.2) supplemented with 100 mg/l of spectinomycin and cultured at 30° C. for 45 hours. AL101, AL107 and ATCC21352/pCG116 were cultured with D-alanine added to the medium to a final concentration of 0.5 g/l. The culture broth thus obtained was subjected to centrifugation and the resulting culture supernatant was checked for the total content of DL-alanine by a high performance liquid chromatography by the OPA postcolumn derivation method and the D- and L-alanine contents by a high performance liquid chromatography using a column (Crown Pack, manufactured by Daicel Chemical Industries, Ltd.). The results are shown in Table 2.

TABLE 2

| Strains | Accumulation of DL-alanine (g/l) | Accumulation of L-alanine (g/l) |
| --- | --- | --- |
| AL101 | 3.0 | 2.5 |
| AL107 | 7.4 | 7.0 |
| ATCC21352/pCG116 | 2.2 | 2.0 |
| BL101 | 4.0 | ND* |
| BL107 | 7.8 | ND |
| ATCC13869/pCG116 | 3.2 | ND |

*: ND, not determined (6) Production of DL-alanine by strain AL1 under limited oxygen supply condition Strain AL1 was cultured for 8 hours in 3 ml of L medium containing 100 mg/l of ampicillin, and the resulting culture broth was inoculated into each of five 300 ml Erlenmeyer flasks charged with 40 ml of A1 medium containing 100 mg/l of ampicillin having a reduced glucose concentration of 1% and cultured at 30° C. with shaking. After 16 hour culture, IPTG, glucose and $(NH_4)_2SO_4$ were added to each flask to final concentrations of 0.1 mM, 2% and 1%, respectively. Thereafter, one of the 5 flasks was continued to be cultured as such, while contents in the remaining 4 flasks were aseptically collected into one flask and were continued to be cultured. Since the medium volume in the latter flask is 4 times larger than that in the former flask, oxygen supply in the latter flask is limited by comparison. After 40 hour culture, DL-alanine content in the culture supernatant was measured in the same manner as described in (3) above. As a result, it was found that DL-alanine was produced in an amount of 3.8 g/l when cultured in 40 ml of the medium, and 8.1 g/l when cultured in 160 ml of the medium.

(7) Production of L-alanine by strain AL107 under limited oxygen supply condition Strain AL107 was inoculated into a 300 ml Erlenmeyer flask charged with 20 ml of NB medium containing 0.5 g/l of D-alanine and 100 mg/l of spectinomycin and cultured at 30° C. for 24 hours with shaking. A 5 ml portion of the resulting culture broth was inoculated into each of three 2 liter Erlenmeyer flasks charged with 200 ml of an A3 medium (40 g of glucose, 10 g of $(NH_4)_2SO_4$, 1 g of $KH_2PO_4$, 0.5 g of $MgSO_4$, 10 mg of $FeSO_4.7H_2O$, 6 mg of $MnSO_4.4–6H_2O$, 30 μg of biotin, 10 g of corn steep liquor, 200 mg of adenine, 2 g of DL-alanine and 20 g of $CaCO_3$ in 1 liter of water, pH 7.2) containing 100 mg/l of spectinomycin and cultured at 30° C. for 24 hours with shaking. The resulting culture broth in three flasks were inoculated respectively into three 5 liter jar fermentors [(a), (b) and (c)] each of which had been charged with 1,650 ml of an A4 medium (65.6 g of glucose, 2.4 g of $(NH_4)H_2PO_4$, 2.5 g of $(NH_4)_2SO_4$, 0.5 g of $MgSO_4$, 10 mg of $CuSO_4.7H_2O$, 10 mg of $MnSO_4.4–6H_2O$, 250 μg of biotin, 600 mg of thiamine hydrochloride, 20 mg of β-alanine, 5 g of corn steep liquor and 4 g of DL-alanine in 1 liter of water, pH 7.2) and had been sterilized. Thereafter, the culture was carried out at an agitation rate of 600 rpm for jar fermentors (a) and (b), and 300 rpm for jar fermentor (c), while keeping the medium pH at 6.8 with ammonia and an aeration rate of 2 liters per minute. When the concentration of residual glucose in the culture medium reached 1 g/l or below, the agitation rate of the jar fermentor (b) was reduced to 300 rpm, while maintaining the agitation rate of the jar fermentor (a) at 600 rpm and that of the jar fermentor (c) at 300 rpm. Starting at this point, a separately sterilized glucose solution was continuously fed into each jar fermenter until the concentration of charged glucose became 20%, and the culture was continued until the concentration of residual glucose in the culture medium reached 1 g/l or below. L-Alanine content in each culture supernatant at the time of the completion of culture was measured in the same manner as described in (5) above and the results are shown in Table 3 together with the culturing periods. In the case of the jar fermentor (c), culture was continued for 96 hours because of a low level of cell growth, but with no success in effecting consumption of glucose to the predetermined concentration level. In each case, the D-alanine content was found to be 0.5 g/l or less. Since supply of oxygen into a culture medium decreases as the agitation rate is reduced, oxygen supply required for sufficient growth of cells cannot be obtained at an agitation rate of 300 rpm [jar fermentor (c)]. However, it was found that the productivity of alanine can be improved by limiting the oxygen supply to an insufficient level for the growth of cells in the course of the culture [jar fermentor (b)].

TABLE 3

| Jar fermentor | Culture period (hr) | Accumulation of L-alanine (g/l) |
| --- | --- | --- |
| (a) | 55 | 32.6 |
| (b) | 70 | 71.0 |
| (c) | 96 | ND |

ND: not determined (8) Purification of L-alanine from AL107 culture broth

A 1 liter portion of the culture broth in the jar fermentor (b) in (7) above was subjected to centrifugation to remove cells, and the resulting culture supernatant was treated with decoloring carbon. The thus treated solution was passed through a column packed with a cation exchange resin, Diaion SK-1B ($H^+$ type) for adsorption of L-alanine. After washing the column with water, elution was carried out with 2N aqueous ammonia. The thus obtained L-alanine fractions were pooled and concentrated. Thereafter, ethanol was added to the concentrate to recover precipitated crystals. By recrystallizing the crystals from ethanol, 55 g of L-alanine crystals were obtained.

According to the present invention, productivity of alanine obtained using *Escherichia coli* strains or strains belonging to the genus Corynebacterium or Brevibacterium can be improved greatly by introducing a microbial L-alanine dehydrogenase gene into these strains and effecting expression of the gene. In addition, since strains belonging to the genus Escherichia, Corynebacterium or Brevibacterium do not produce odor-producing materials which are produced in the case of using Arthrobacter sp. HAP1, DL-, L- or D-alanine can be easily purified from the culture medium.

While the invention has been described in detail and with reference to specific examples thereof, it will be apparent to one skilled in the art that various changes and modifications can be made therein without departing from the spirit and scope thereof.

All documents cited above are incorporated in their entirety by reference.

What is claimed is:

1. A process for producing alanine which comprises culturing in a medium containing glucose for a carbon source a microorganism belonging to the genus Escherichia, Corynebacterium or Brevibacterium which is capable of producing alanine and harbors a recombinant DNA containing the gene coding for L-alanine dehydrogenase which is cloned from Arthrobacter sp. HAP1, under conditions such that alanine is produced and accumulated in the culture medium, and recovering alanine from said culture medium.

2. The process for producing alanine according to claim 1, wherein said alanine is DL-alanine, L-alanine or D-alanine.

3. The process for producing alanine according to claim 1, wherein said microorganism is selected from the group consisting of *Escherichia coli* and *Corynebacterium glutamicum* which are capable of producing alanine and harbor a recombinant DNA containing the gene coding for L-alanine dehydrogenase which is derived from Arthrobacter sp. HAP1, and wherein said culturing is under an oxygen-supply limited condition.

4. A microorganism belonging to the genus Escherichia, Corynebacterium or Brevibacterium which is capable of producing alanine and harbors a recombinant DNA containing the gene coding for L-alanine dehydrogenase which is cloned from Arthrobacter sp. HAP1.

5. A method of producing L-alanine dehydrogenase which comprises culturing the microorganism according to claim 4 under conditions such that the DNA coding for L-alanine dehydrogenase is expressed and L-alanine dehydrogenase is produced, and recovering L-alanine dehydrogenase therefrom.

6. An isolated DNA fragment encoding L-alanine dehydrogenase, which is cloned from Arthrobacter sp. HAP1.

7. A recombinant DNA comprising the DNA fragment according to claim 6 and a vector DNA.

8. A process of producing alanine which comprises culturing in a medium containing glucose as a carbon source a microorganism belonging to the genus Escherichia, Corynebacterium or Brevibacterium that contains a recombinant DNA encoding Arthrobacter sp. HAP1 L-alanine dehydrogenase under conditions such that alanine is produced and accumulated in the culture medium, and isolating said alanine.

* * * * *